(12) United States Patent
Yan et al.

(10) Patent No.: US 12,161,312 B2
(45) Date of Patent: Dec. 10, 2024

(54) SHEATH, SURGICAL ASSEMBLY AND METHOD OF USING THE SAME

(71) Applicant: INNOVEX MEDICAL CO., LTD, Shanghai (CN)

(72) Inventors: Hang Yan, Shanghai (CN); Zhongwei Zheng, Shanghai (CN); Luobin Liu, Shanghai (CN); Yundong Liu, Shanghai (CN)

(73) Assignee: INNOVEX MEDICAL CO., LTD, Shanghai (CN)

( * ) Notice: Subject to any disclaimer, the term of this patent is extended or adjusted under 35 U.S.C. 154(b) by 501 days.

(21) Appl. No.: 17/609,976

(22) PCT Filed: Apr. 30, 2020

(86) PCT No.: PCT/CN2020/088150
§ 371 (c)(1),
(2) Date: Nov. 9, 2021

(87) PCT Pub. No.: WO2021/217566
PCT Pub. Date: Nov. 4, 2021

(65) Prior Publication Data
US 2022/0202408 A1 Jun. 30, 2022

(51) Int. Cl.
*A61B 17/02* (2006.01)
*A61B 17/00* (2006.01)

(52) U.S. Cl.
CPC *A61B 17/0218* (2013.01); *A61B 2017/00557* (2013.01)

(58) Field of Classification Search
CPC ...... A61B 17/0218; A61B 2017/00557; A61B 17/3439; A61B 17/0293
USPC .................................................. 600/184–245
See application file for complete search history.

(56) References Cited

U.S. PATENT DOCUMENTS

| 2008/0300544 A1* | 12/2008 | Palm | A61M 25/0662 |
| | | | 604/164.03 |
| 2017/0035460 A1* | 2/2017 | Bonutti | A61M 25/0662 |

FOREIGN PATENT DOCUMENTS

CN 104706458 A 6/2015

* cited by examiner

*Primary Examiner* — Eduardo C Robert
*Assistant Examiner* — Tara Rose E Carter
(74) *Attorney, Agent, or Firm* — NZ CARR LAW OFFICE

(57) ABSTRACT

A sheath includes: a ring-shaped inner layer structure, a ring-shaped outer layer structure and a frame structure, which can be radially expanded with the inflation of a balloon inside the inner layer structure. When the inner layer structure, the frame structure and the outer layer structure are not radially expanded, a radial dimension of an inner channel of the inner layer structure is at a first radial dimension, and the first radial dimension is greater than or equal to a radial dimension of the balloon that is not inflated. After the inner layer structure, the frame structure, and the outer layer structure are radially expanded, and the balloon is removed or deflated, the radial dimension of the inner channel of the inner layer structure is at a second radial dimension, and the second radial dimension is greater than the first radial dimension.

16 Claims, 9 Drawing Sheets

SHEATH, SURGICAL ASSEMBLY AND METHOD OF USING THE SAME

TECHNICAL FIELD

The present invention relates to the technical field of medical instruments, and more specifically, to a sheath, a surgical assembly and a method of using the same.

BACKGROUND

In the field of medical equipment, the sheath can be used to form the required working channel, which can be used for percutaneous nephroscopy, biliary surgery, etc.; taking the percutaneous nephroscope channel of percutaneous nephroscopy as an example, after the puncture is completed, the inflated balloon can be used to open the punctured physiological channel, and the sheath can be fed in following the inflated balloon, thereby forming a percutaneous nephroscope channel by using the sheath.

However, if the inner diameter of the sheath does not match the outer diameter of the balloon after inflation, it is easy to damage the human body and/or affect the performance of percutaneous nephroscopy; for example, if the outer diameter of the balloon is too small, there will be a gap between the sheath and the balloon, which is likely to cause damage to the internal organs; and for example, if the outer diameter of the balloon is too large, the sheath cannot enter smoothly. It can be seen that in prior art, the effect in establishing the working channel and the safety during the establishment process both depend on the control of the inflation size of the balloon, which is difficult to be effectively guaranteed. Further, based on the surgical assembly in the prior art, the sheath has to be inserted again, and the insertion process may easily cause secondary damage to the tissue.

SUMMARY

The present invention provides a sheath, a surgical assembly of percutaneous nephroscopy and a method of using the same, so as to solve the problem of difficulty in guaranteeing the effect in establishing the working channel and the safety during the establishment process and of being likely to cause secondary damage.

According to a first aspect of the present invention, a sheath is provided, including a ring-shaped inner layer structure, a ring-shaped outer layer structure and a frame structure, wherein the outer layer structure is arranged around an outer side of the inner layer structure, and the frame structure is arranged between the inner layer structure and the outer layer structure; the inner layer structure, the frame structure, and the outer layer structure can be radially expanded with the inflation of a balloon inside the inner layer structure;
  when the inner layer structure, the frame structure and the outer layer structure are not radially expanded, a radial dimension of an inner channel of the inner layer structure is at a first radial dimension, and the first radial dimension is greater than or equal to a radial dimension of the balloon that is not inflated;
  after the inner layer structure, the frame structure, and the outer layer structure are radially expanded, and the balloon is removed or deflated, the radial dimension of the inner channel of the inner layer structure is at a second radial dimension, and the second radial dimension is greater than the first radial dimension.

Optionally, the frame structure includes at least one ring-shaped frame body, the frame body includes at least one deformable section, a deformation degree of the deformation section is related to a circumferential length of the frame body.

Optionally, the deformable section is an arc line section or a broken line section when the frame body is not expanded, the deformable section is an arc line section or a broken line section when the frame body is expanded, and a length of the deformable section along the circumferential direction of the frame body matches a bending degree or a curving degree of the deformable section, wherein
  when the frame body is radially expanded, the bending degree or curing degree of the deformable section becomes lower, and a length of the deformable section along the circumferential direction of the frame body becomes longer.

Optionally, the frame body is formed by connecting a plurality of deformable sections end to end in sequence.

Optionally, if the deformable section is the broken line section, the frame body has a continuous sawtooth waveform;
  if the deformable section is the arc line section, the frame body has a continuous sinusoidal waveform.

Optionally, an opening direction of the deformable section matches an axial direction of the frame body, and the opening directions of two adjacent deformable sections in the same frame body are opposite.

Optionally, the frame structure further includes a reinforcing rib connected between two adjacent frame bodies, the reinforcing rib is connected to axial end portions of the two deformable sections along the axial direction of the frame body, and the openings of the two deformable sections connected to the reinforcing rib are in opposite directions.

The inner layer structure includes an inner layer film;
  a material of the inner layer film is any one of PTFE, silica gel, or polyurethane material;
  the outer layer structure includes an outer layer film;
  a material of the outer layer film is any one of PTFE, silica gel, or polyurethane material.

Optionally, a material of the frame structure is at least one of cobalt-based alloy, stainless steel and platinum-chromium alloy.

The frame structure is formed by at least one of:
  laser cutting;
  first forming a structure that forms a sine wave or sawtooth wave that is not in a closed loop by mechanical processing, then welding end to end to form a ring-shaped frame body, and then selecting one or more welding points to weld a plurality of frame bodies together, to form the frame structure;
  first forming the spiral-shaped frame body to be required by mechanical processing, and selecting one or more welding points for a plurality of frame bodies together if the number of the spiral-shaped frame body is at least a plurality of frame bodies, to form the frame structure.

According to a second aspect of the present invention, a surgical assembly is provided, including the sheath according to the first aspect and optional solutions thereof, the balloon and a balloon catheter, wherein the balloon is arranged at the balloon catheter, and an inner cavity of the balloon is communicated with an inner cavity of the balloon catheter.

According to a third aspect of the present invention, a method of using the surgical assembly according to the second aspect is provided, including:

filling the balloon through the balloon catheter to inflate the balloon when both the sheath and the balloon in the sheath reach a target position;

controlling the balloon to deflate and taking out the balloon and the balloon catheter after the sheath is expanded with the inflation of the balloon to use the inner channel of the second radial dimension in the sheath as a currently-established working channel.

For the sheath, the surgical assembly and the method of using the same provided by the present invention, since the radial size of the sheath is variable, the sheath is facilitated to wrap the balloon and enter the human body when being not expanded, and to expand with the inflation of the balloon after reaching the target position, thereby realizing the establishment of the channel. It can be seen that when the sheath related to the present invention is used, the effect in establishing the working channel and the safety during the establishment process may not be limited to the control of the inflation size of the balloon, thereby effectively guaranteeing the safety and the effect in establishing the channel. Moreover, based on the sheath and the surgical assembly involved in the present invention, the two-step action of expanding and inserting the sheath is facilitated to be changed into one-step action and further to directly establish the working channel after the expansion, thereby simplifying the work process, avoiding secondary damage (such as tissue tear damage) caused by the two-step action and further improving the safety.

BRIEF DESCRIPTION OF THE DRAWINGS

In order to describe the embodiments of the present invention or the technical scheme in the prior art more clearly, brief introduction on drawings needed to be used in the embodiment will be made below. It is obvious that the drawings described below are merely some embodiments of the present invention, and those skilled in the technical field further can obtain other drawings according to the drawings without creative efforts.

DESCRIPTION OF REFERENCE NUMERALS

1—Outer layer structure;
2—Inner layer structure;
3—Frame structure;
31—Frame body;
311—Deformable section;
312—Transition section;
32—Reinforcing rib.

DETAILED DESCRIPTION OF THE EMBODIMENTS

Clear and intact description will be made on technical schemes in the embodiments of the present invention below in combination with drawings in the embodiments of the present invention. Obviously, the described embodiments are merely a part of embodiments of the present invention and are not all the embodiments. Based on the embodiments of the present invention, all the other embodiments obtained by those of ordinary skill in the art without inventive effort are within the scope of the present invention.

Terms "first", "second", "third", "fourth", and the like (if any) in the specification and claims of the present invention and the foregoing accompanying drawings are used to distinguish similar objects, but do not need to be used for describing a specific sequence or an order. It should be understood that data used in this way can be interchanged under appropriate circumstances, so that the embodiments of the present invention described herein can be implemented in an order other than those illustrated or described herein. In addition, terms "including", "having", and any variations thereof are intended to cover non-exclusive inclusions, for example, processes, methods, systems, products, or devices that contain a series of steps or units need not be limited to those clearly listed steps or units, but may include other steps or units not explicitly listed or inherent to these processes, methods, products, or devices.

The technical solutions of the present invention are described in detail below with reference to the specific embodiments. The following several embodiments may be combined with each other, and a same or similar concept or process may not be described again in some embodiments.

Figure 1:
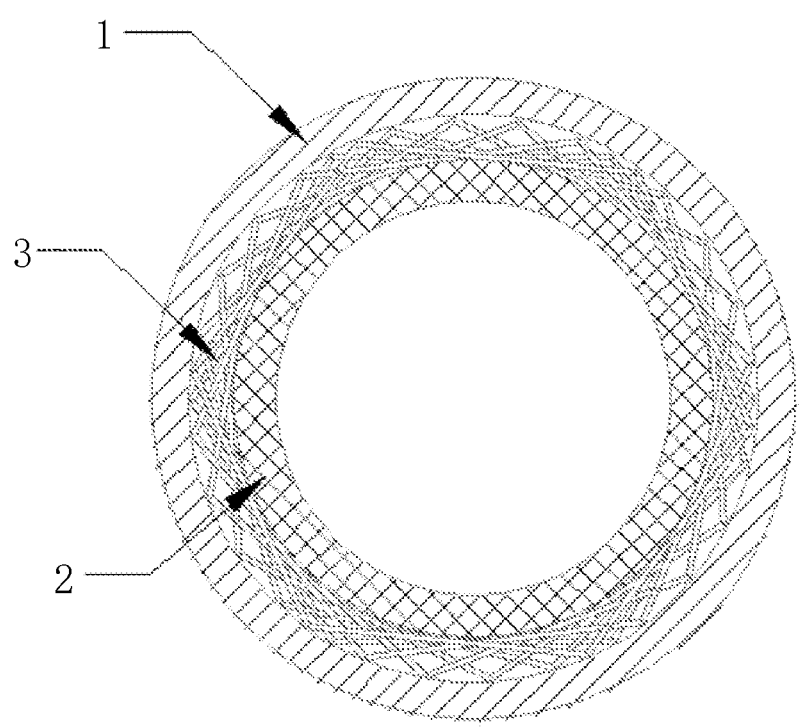
FIG. 1 is a schematic cross-section structural view of a sheath according to an embodiment of the present invention.

With reference to FIG. 1, a sheath includes a ring-shaped inner layer structure 2, a ring-shaped outer layer structure 1 and a frame structure 3, wherein the outer layer structure 1 is arranged around an outer side of the inner layer structure 2, and the frame structure 3 is arranged between the inner layer structure 2 and the outer layer structure 1; the inner layer structure 2, the frame structure 3, and the outer layer structure 1 may be radially expanded with the inflation of a balloon (not shown) inside the inner layer structure 2, or in other examples may be radially expanded with the radial changes of other components inside the inner layer structure 2, which is not limited for the balloon.

When the inner layer structure 2, the frame structure 3 and the outer layer structure 1 are not radially expanded, a radial dimension of an inner channel of the inner layer structure 2 is at a first radial dimension, wherein the fact of being not radially expanded may be a fact of not being expanded with the inflation of the balloon, and further, the radial dimension under the fact of being not radially expanded may be at a limit position where the frame structure 3 is compressed at or may not be at the limit position.

After the inner layer structure 2, the frame structure 3, and the outer layer structure 1 are radially expanded, and the balloon is removed or deflated, the radial dimension of the inner channel of the inner layer structure is at a second radial dimension.

The first radial dimension is greater than or equal to a radial dimension of the balloon that is not inflated, and further, all the radial dimensions or the ranges of radial dimension that meet the requirement may be understood as the first radial dimension mentioned above. It can be seen that the above may refer to a certain value or certain specific values, and may also refer to a certain size range, which is not limited to a specific value.

The second radial dimension may be understood as any dimensions larger than the first radial dimension, and specifically may refer to a dimension required for establishing the working channel (for example, a percutaneous renal channel). The second radial dimension may refer to a certain value or certain specific values, and may also refer to a certain size range, which is not limited to a specific value. In addition, the second radial dimension may be a corresponding radial dimension after the balloon is inflated, or may be a radial dimension that is reduced to a certain extent after the inflation with the inflation of the balloon. No matter what kind of change, these may not deviate from the description of the second radial dimension in the embodiment of the present invention.

The inner layer structure 2 can be understood as a ring-shaped structure, which may be adapted to contact with the balloon, and may expand in the surface area with the inflation of the balloon.

The outer layer structure 1 can be understood as a ring-shaped structure, which may be adapted to contact with the physiological channel, and may indirectly expand in the surface area with the inflation of the balloon.

The frame structure 3 may be understood as a structure that may be radially expanded under force and may maintain the inflation result, which in other words may provide sufficient radial support during inflation and may be used as a stable working channel (for example, percutaneous renal channel). The ability to undergo radial expansion under force and the ability to maintain the expansion result may be determined by the structural principle of the frame structure 3 and/or the material used.

It can be seen that since the radial size of the sheath is variable, the sheath is facilitated to wrap the balloon and enter the human body when being not inflated, and to expand with the inflation of the balloon after reaching the target position, thereby realizing the establishment of the channel. It can be seen that when the sheath related to the embodiment of the present invention is used, the effect in establishing the working channel and the safety during the establishment process may not be limited to the control of the inflation size of the balloon, thereby effectively guaranteeing the safety and the effect in establishing the channel.

Moreover, the frame structure 3 may be prevented from directly acting on the human body and the balloon through the inner layer structure and the outer layer structure, so that the safety is guaranteed, and the in and out of the sheath and the balloon may be realized smoothly.

It is also to be noted that since one of the creative contributions of the embodiments of the present invention is (due to the actual needs in the process of establishing the channel) the idea that the radial dimension of the sheath may be changed while introducing a three-layer structure to achieve the idea, regardless of the manner in which the inner layer structure 2, the outer layer structure 1 and the frame structure are matched with the creative contribution, they do not deviate from the description of the embodiment of the present invention.

In an embodiment, the inner layer structure 2 includes an inner layer film, and the inner layer film is a stretchable polymer film. Through the polymer membrane, the inner layer structure may be tightly wrapped on the outer wall of the balloon and may be expanded simultaneously while the balloon is inflated, and the inner layer film may maintain close contact with the outer wall of the balloon during the inflation process of balloon. In a specific example, the material of the inner film may be elastic materials such as polyurethane (TPU) and silicone, or may be PTFE.

In addition, the inner layer structure 2 and the frame structure 3 may be fixedly connected at some positions, or may not be fixedly connected. For example, if the material of the inner layer film is not prone to shrinking deformation after the expansion, the inner layer structure 2 and the frame structure 3 may not be fixedly connected with each other, otherwise, fixedly connected at some points with each other.

In an embodiment, the outer layer structure 1 includes an outer layer film, and the outer layer film is a PTFE film. In other examples, the outer layer film may also be silica gel, polyurethane, or the like.

PTFE, specifically Poly tetra fluoroethylene, may be understood as polytetrafluoroethylene. Further, the excellent surface smoothness of PTFE material is used to reduce the exit resistance of the sheath after the operation.

In actual implementation, the inner and outer films may be fixed with the frame structure by dipping, hot melting, sewing and gluing.

With reference to FIGS. 2 to 11, in an embodiment, the frame structure 3 includes at least one ring-shaped frame body 31, and further, the expansion of the frame structure 3 may also be understood as the expansion of the frame body 31; the frame body 31 includes at least one deformable section 311, and a deformation degree of the deformation section is related to a circumferential length of the frame body.

In an embodiment, the deformable section 311 is an arc line section or a broken line section when the frame body 31 is not expanded, and the deformable section 311 is an arc line section or a broken line section when the frame body 31 is expanded, wherein there are some possibilities: the deformable section is a broken line section both when the frame body is not expanded and expanded, the deformable section is an arc line section both when the frame body is not expanded and expanded, the deformable section is an arc line section both when the frame body is not expanded and is a broken line section when the fame body is expanded, and the deformable section is a broken line section both when the frame body is not expanded and is an arc line section when the frame body is expanded, etc.

The arc line section refers to that the line section is formed by at least one circular arc line portion, and the center of curvature of the at least one circular arc line portion is located on the same side of the arc line section;

The broken line section refers to being formed by connecting two line section portions together, wherein the junction of the two line section portions may form an included angle, and the included angle may have a certain chamfer; in addition, when the chamfer is a rounded corner and the size of the rounded corner is configured to a certain value, the broken line section may also be regarded as an arc line section, i.e., the arc line section may also be regarded as a type of the broken line section. In the examples of FIGS. 2 to 10, the deformable section 311 may be understood as the broken line section.

With reference to FIGS. 2 to 11, a length of the deformable section 311 along the circumferential direction of the frame body matches a bending degree or a curving degree of the deformable section 311; specifically, if the deformable section is the arc line section, the larger the corresponding curvature, the smaller the radius of curvature, indicating a larger bending degree; if the deformable section is the broken line section, the smaller the corresponding included angle, the higher the bending degree.

When the frame body 31 is radially expanded, the bending degree or curing degree of the deformable section 311 becomes lower, and a length of the deformable section 311 along the circumferential direction of the frame body 31 becomes longer.

When the balloon is inflated, a radial expansion force F1 is generated on the frame body 31, and at the same time, the physiological channel may generate a radially-restricting expansion force F2 on the frame body 31; as the balloon inflates, F1 becomes larger, and when a force difference of F1−F2 is greater than a certain degree (for example, F0), the frame body 31 may be expanded, wherein F0 may be regarded as a threshold value associated with the material of the frame body 311;

The frame body 31 may be configured to change the size of the frame body inwardly and outwardly due to the applied force, and then a frame body with a suitable material and/or structure may be selected so that F2 may never be greater than F0 and F1−F2 may be greater than F0 as the balloon inflates. Since the resistance to deformation under different materials and/or structures is known or measurable and the force F2 generated by the physiological channel and the force F1 generated by the balloon may also be determined by limited experiments or theoretical calculations, those skilled in the art can obtain specific technical solutions under the concept of the above embodiments; The frame body 31 may also be configured to only change the size of the frame body in the radially outward direction.

In other examples, elastic components (such as springs, elastic sheets, torsion springs, etc.) may further be configured in the frame body 31, and other components that match the elastic components to achieve corresponding functions may further be configured, wherein the elastic component may provide an expanding force F3 so that F2 needs to be greater than F3+F0 to realize radial decrease, and F1 only needs to be greater than F0−F3 to make radial expansion.

The frame body 31 may be any metal materials or composite materials that may expand under the inflation of the balloon for satisfying the relevant analysis of the force in the previous article and further facilitate enhancing the structural strength to maintain the shape after expansion, which are not limited by the following examples.

In a specific example, the frame body 31 may be made of at least one of metal materials such as cobalt-based alloy, stainless steel, and platinum-chromium alloy.

In a specific example, the frame structure 3 may be processed by laser cutting and other processes, and may also be formed by other processing techniques such as first forming a structure that forms a structure that is not in a closed loop (e.g., a sine wave or sawtooth wave structure) by mechanical processing, then welding end to end to form a ring-shaped frame body 31, and then selecting one or more welding points to weld a plurality of frame bodies 31 together to form the frame structure 3, and such as first forming the spiral-shaped frame body 31 to be required by mechanical processing, and selecting one or more welding points for a plurality of frame bodies together to form the frame structure 3.

Figure 10:
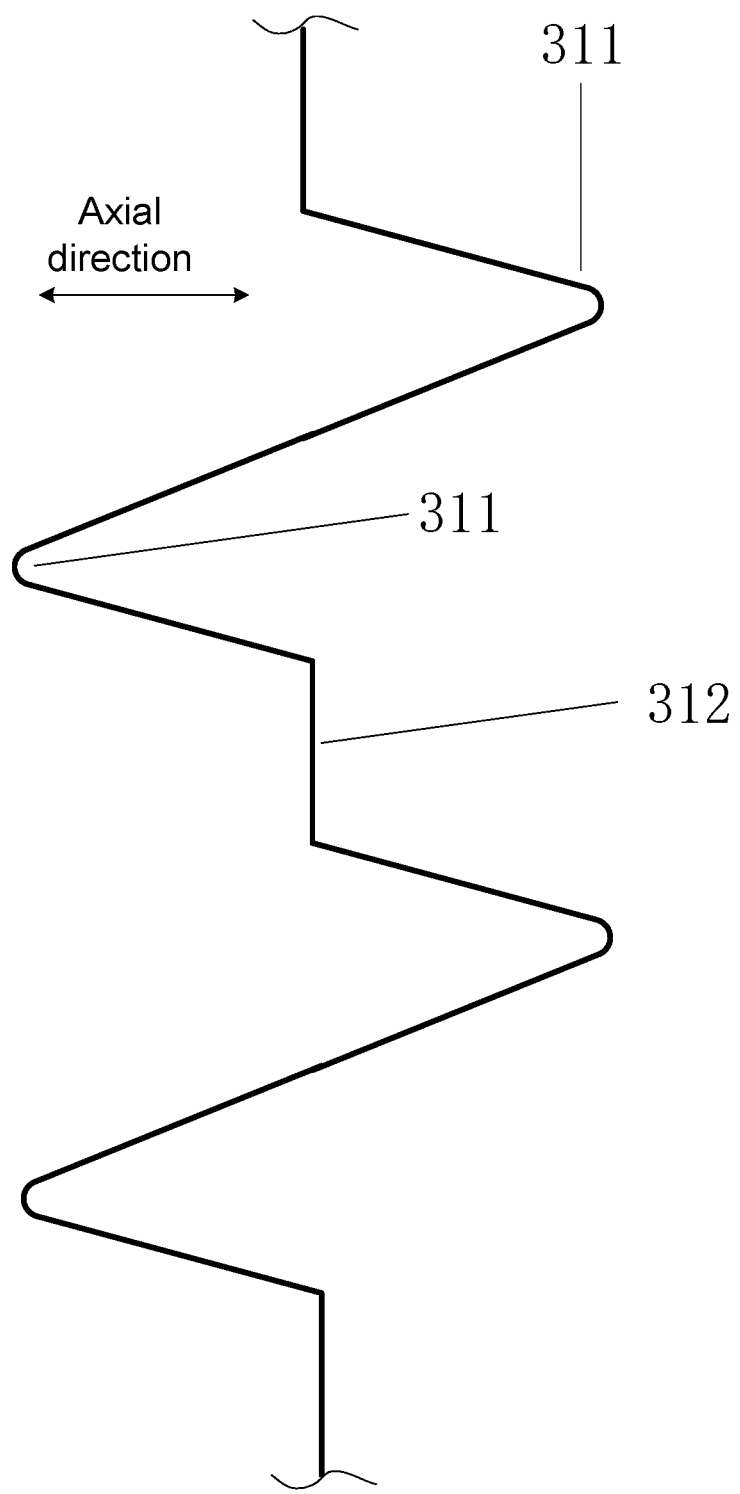
FIG. 10 is a partial structural view of another frame body according to an embodiment of the present invention.

In an embodiment, as shown in FIGS. 2 to 9 and FIG. 11, the frame body 31 is formed by connecting a plurality of deformable sections 311 end to end in sequence; in other embodiments, taking FIG. 10 as an example, a transition section 312 may be connected between part or all of the adjacent deformable sections 311, and the transition section 312 may be arranged along the circumference of the frame body 31, for example.

Figure 11:
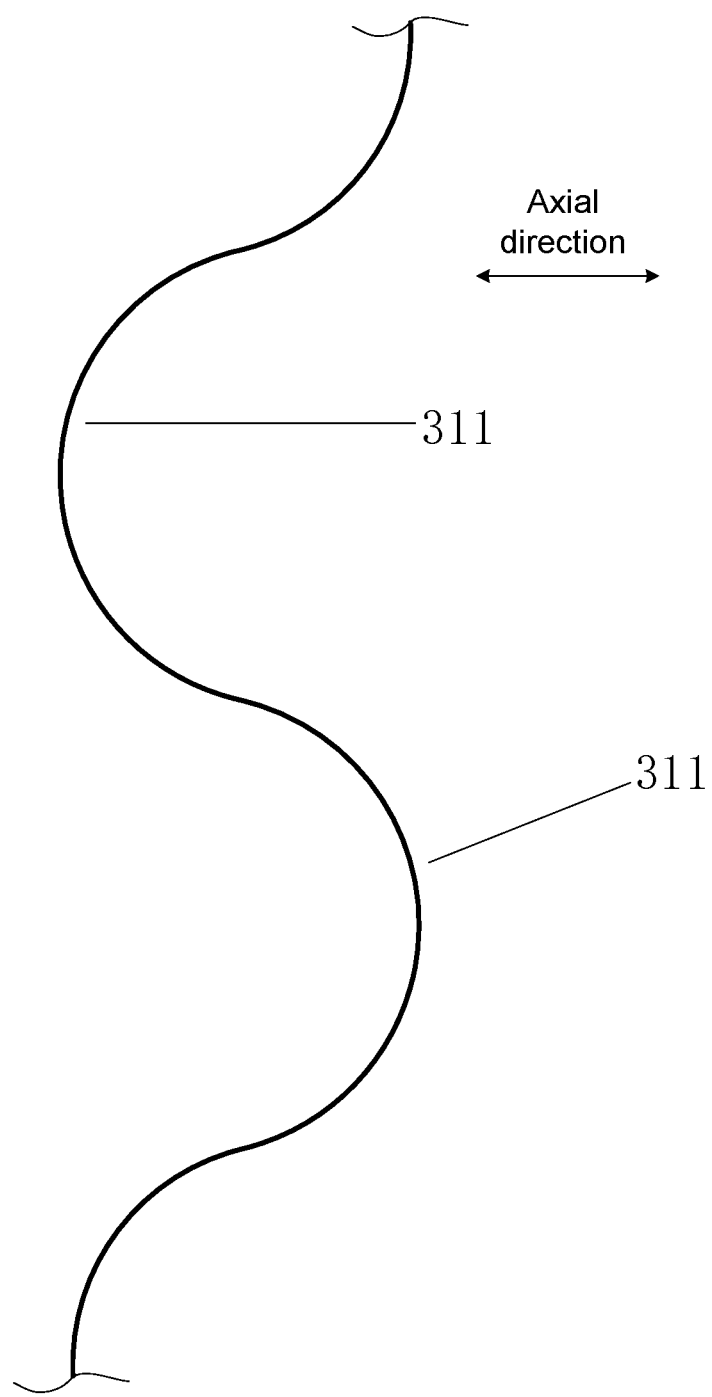
FIG. 11 is a partial structural view of a still another frame body according to an embodiment of the present invention.

If the deformable section 311 is the broken line section, the frame body has a continuous sawtooth waveform, as shown in FIGS. 2 to 9; if the deformable section 311 is the arc line section, the frame body has a continuous sine waveform, as shown in FIG. 11.

Since a continuous waveform may be formed, each deformable section 311 may also be understood as a waveform, and further, each waveform may have peaks and troughs correspondingly, and the peaks and troughs may be understood as the end portion of the deformable section along the axial direction.

In addition to the broken line section and the arc line section shown in FIGS. 1 to 10, the deformable section 311 may also be a spiral section. The deformable section used by a single frame body may have one type or multiple types, for example, including at least two of a broken line section, an arc line section, and a spiral section.

In an embodiment, an opening direction of the deformable section 311 matches an axial direction of the frame body; in other words, the deformable section 311 is undulating in the axial direction, which includes the situation that it undulates completely in the axial direction, and also the situation that has a certain deflection relative to the axial direction, which may prevent the deformation from affecting the radial dimension. The embodiment of the present invention also does not exclude an embodiment in which the opening direction of the deformable section 311 has a certain deflection in the radial direction or relative to the radial direction.

For the opening direction, for example, if the deformable section 311 is the broken line section, the direction of the bisector of the acute angle of the broken line section may represent the opening direction; if the deformable section 311 is the arc line section, the direction of the bisector of the arc (less than 180 degrees of arc) of the arc line section may represent the opening direction.

In an embodiment, the opening directions of two adjacent deformable sections in the same frame body are opposite, and furthermore, the crests and troughs mentioned above may be formed.

In an embodiment, the frame structure 3 further includes a reinforcing rib 32 connected between two adjacent frame bodies 31, the reinforcing rib 32 is connected to axial end portions of the two deformable sections 311 along the axial direction of the frame body 31, and the openings of the two deformable sections connected to the reinforcing rib 32 are in opposite directions.

The reinforcing rib 32 may only be arranged between some parts of deformable sections 311, instead of connecting the reinforcing rib 32 between all the deformable sections 311 that satisfy the above description; at the same time, the embodiment of the present invention does not exclude the embodiment in which all the deformable sections 311 are connected to the reinforcing rib 32.

The deformable sections 311 are connected together by the reinforcing rib 32, which may provide better structural stability.

Figure 2:
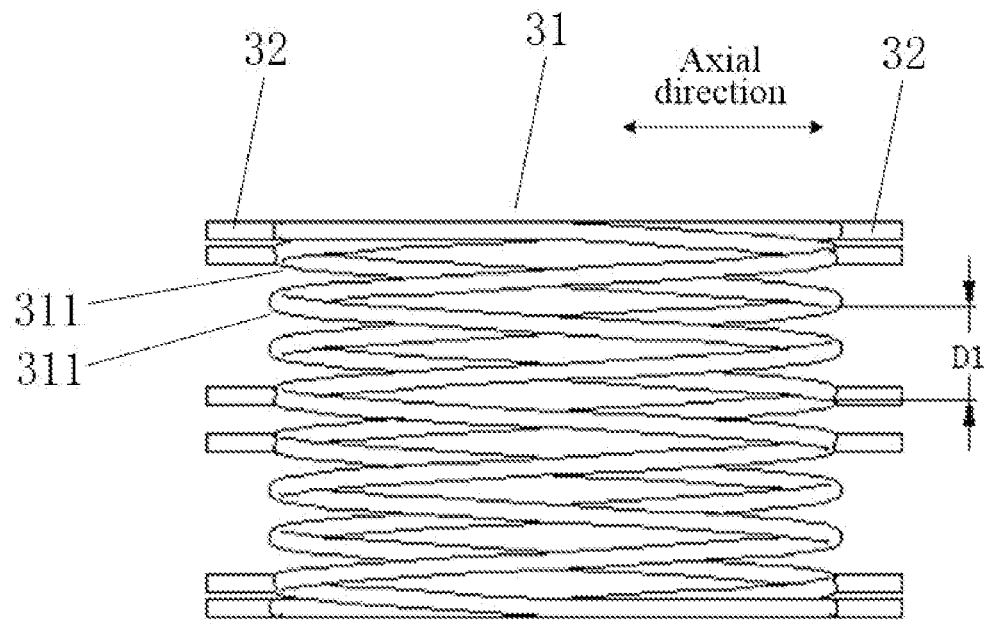
FIG. 2 is a schematic diagram one of the structure when the frame body is not expanded according to an embodiment of the present invention.
Figure 3:
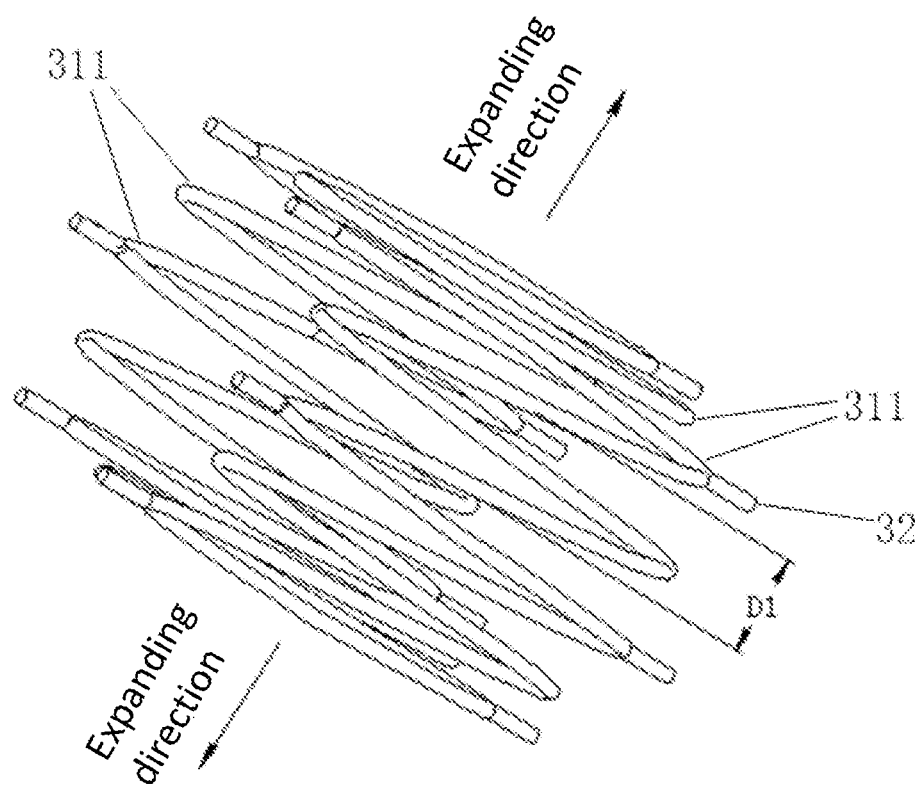
FIG. 3 is a schematic diagram two of the structure when the frame body is not expanded according to an embodiment of the present invention.
Figure 4:
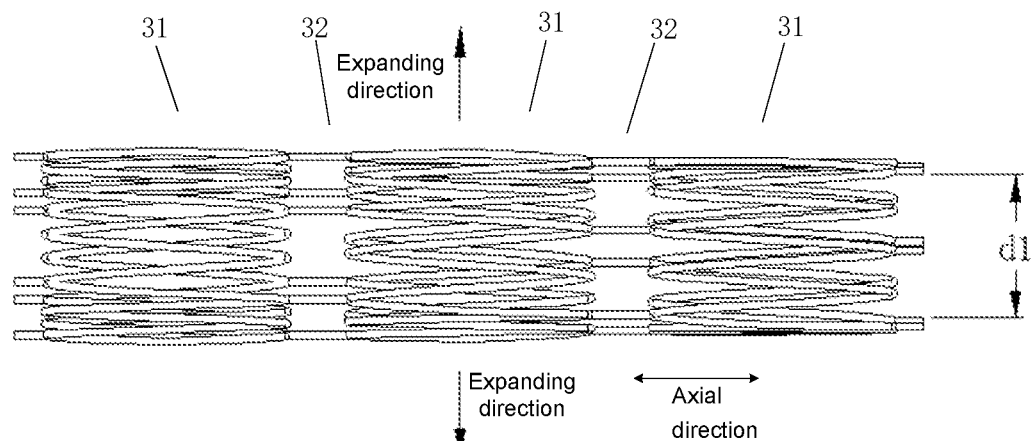
FIG. 4 is a schematic diagram one of the structure when the frame structure is not expanded according to an embodiment of the present invention.
Figure 5:
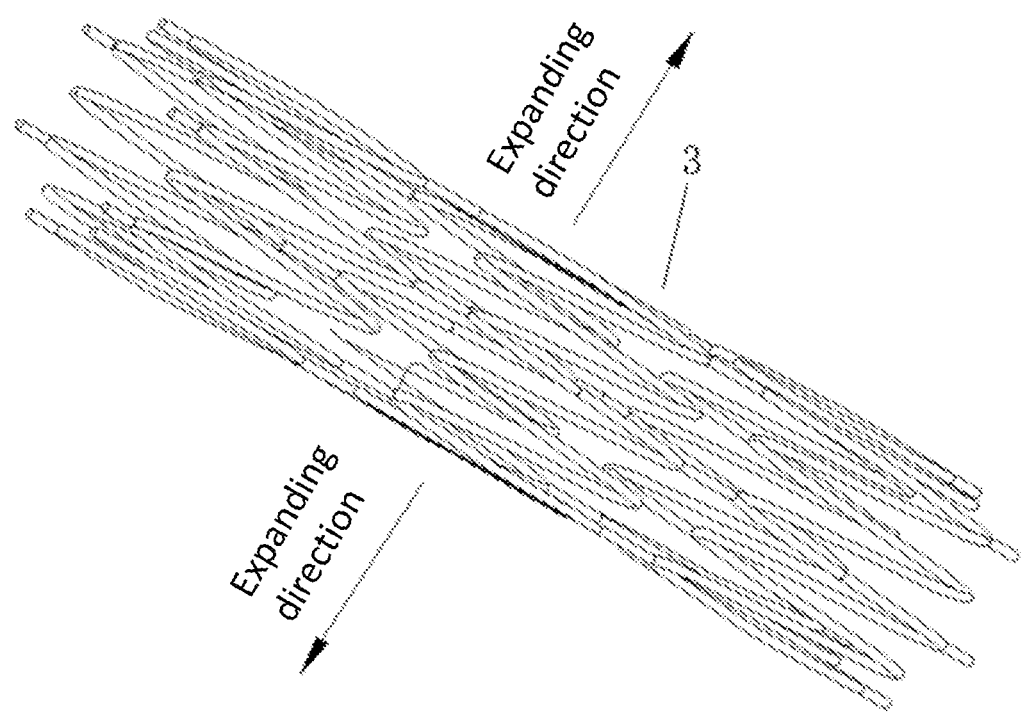
FIG. 5 is a schematic diagram two of the structure when the frame structure is not expanded according to an embodiment of the present invention.
Figure 6:
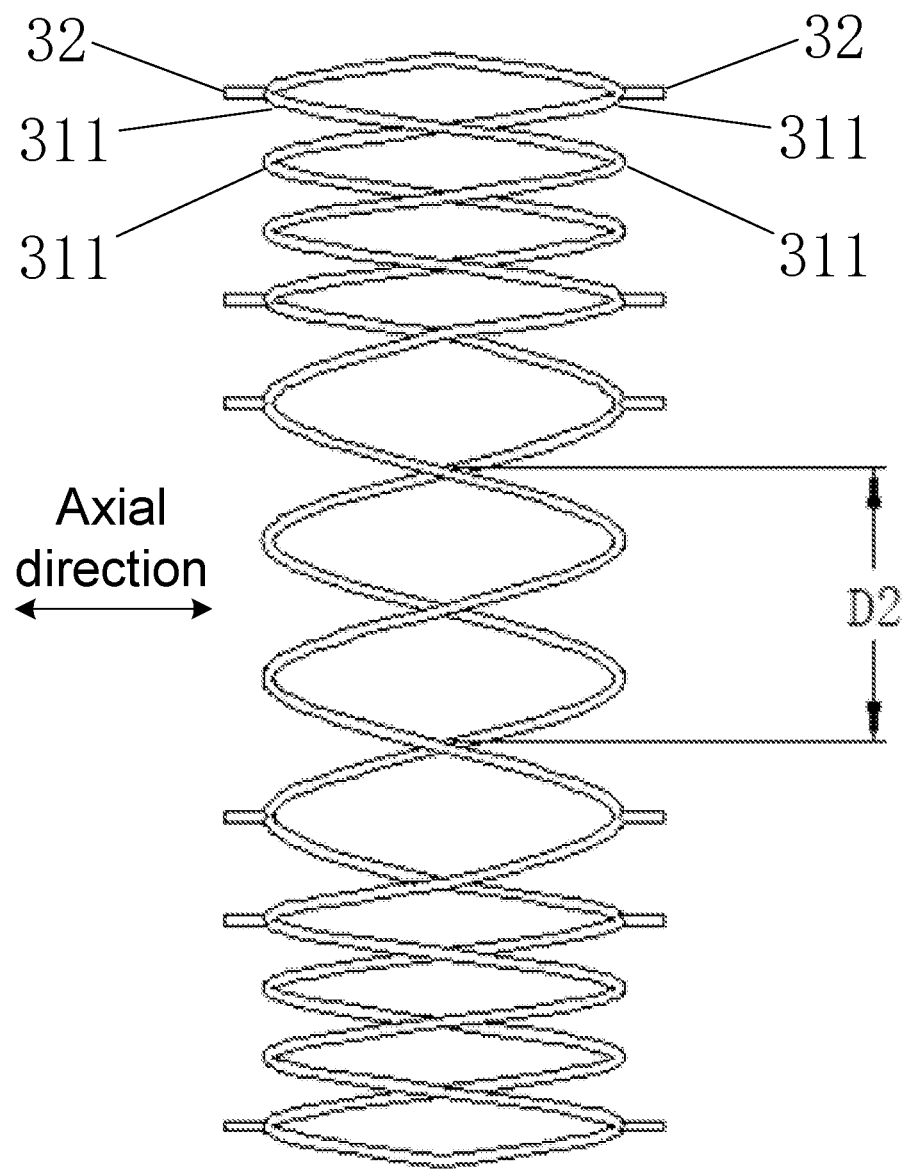
FIG. 6 is a schematic diagram one of the structure after the frame body is expanded according to an embodiment of the present invention.
Figure 7:
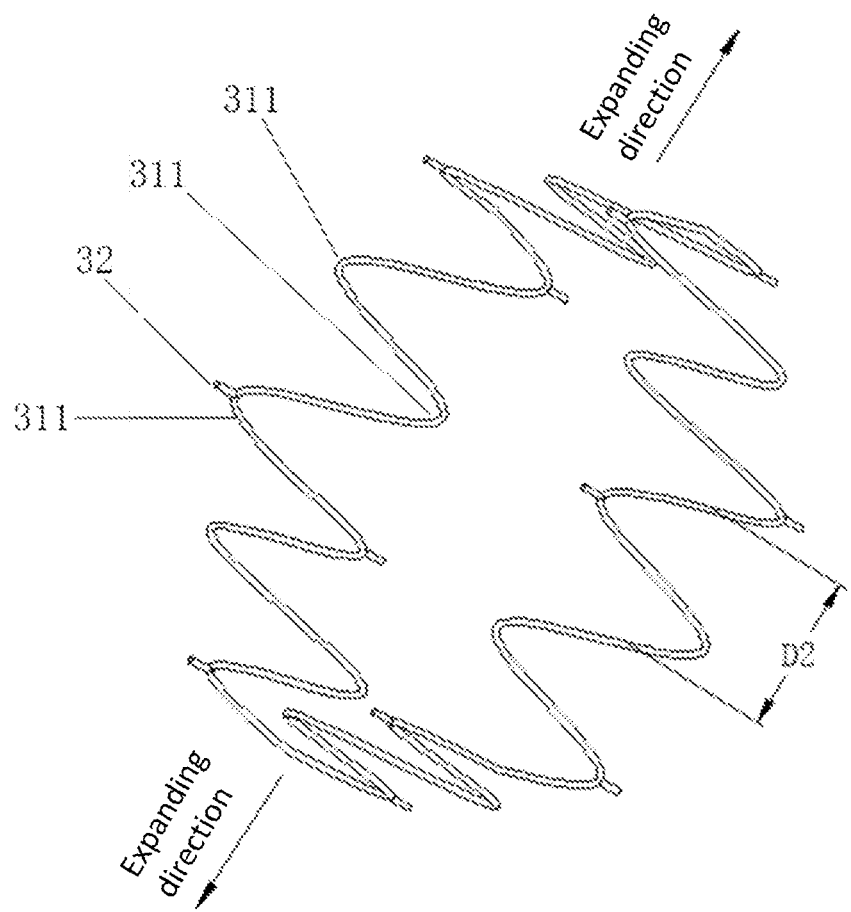
FIG. 7 is a schematic diagram two of the structure after the frame body is expanded according to an embodiment of the present invention.
Figure 8:
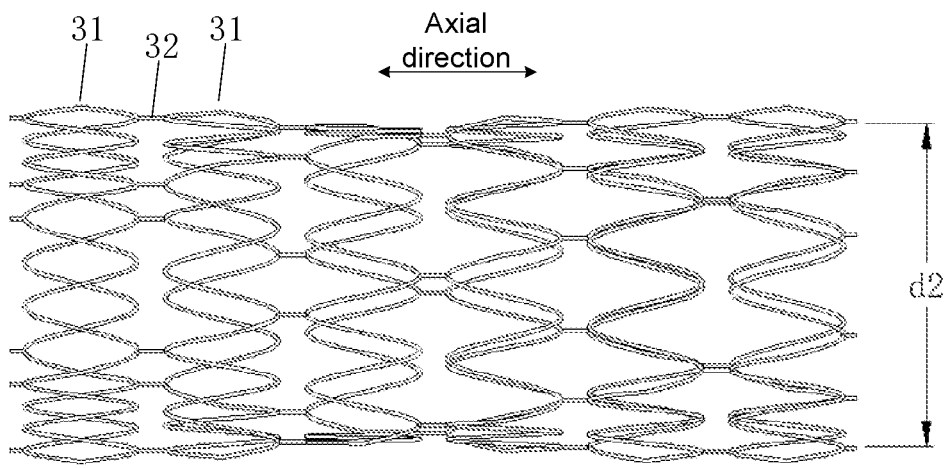
FIG. 8 is a schematic diagram one of the structure after the frame structure is expanded according to an embodiment of the present invention.
Figure 9:
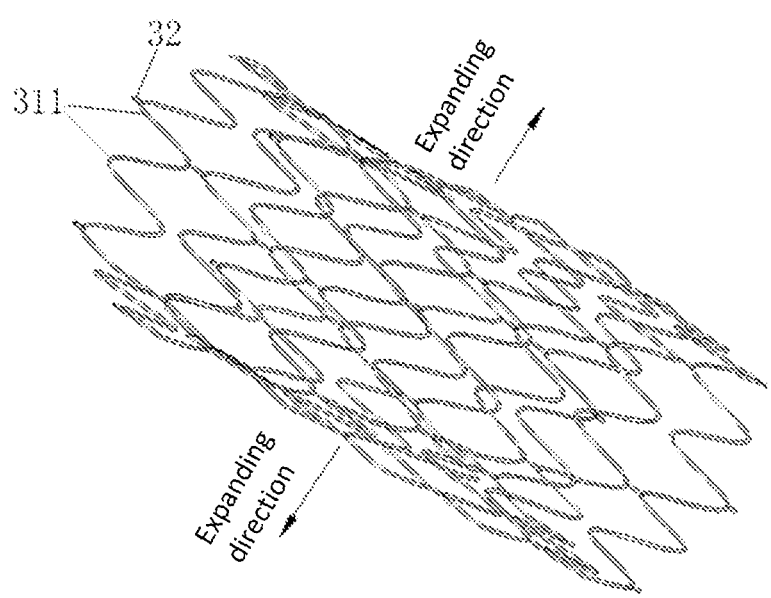
FIG. 9 is a schematic diagram two of the structure after the frame structure is expanded according to an embodiment of the present invention.

With reference to the circumferential length D1 in FIGS. 2 and 3 and the circumferential length D2 in FIGS. 6 and 7, it can be known that the deformable sections 311 are connected together by the reinforcing rib 32 to provide better structural stability; with reference to the diameter d1 in FIG. 4 and the diameter d2 in FIG. 8, the radial dimension of the entire frame body 31 may be enlarged due to the extension of the circumferential length.

Specifically, if the continuous deformable section is regarded as a waveform and one fluctuation is regarded as a cycle of waveform, the circumferential length of the waveform increases with the radial expansion, the circumferential length of the waveform after expansion is D2, the process of radial expansion of the frame body 31 with the inflation of the balloon is similar to the process of inflating a folding umbrella, and the circumferential length of the waveform in a single cycle after expansion is greater than the circumferential length of the waveform in a single cycle before expansion, i.e., D2>D1. The inner diameter d2 of the frame body 31 after expansion may be the diameter of the balloon after inflation, and then: d2>d1.

In addition to the frame structure 3 shown in FIGS. 1 to 10, in other embodiments, the frame structure 3 may also select one or more spiral structures, which may be understood as a spiral-shaped structure with a variable spiral inner diameter, with an axis matching the axis of the inner structure and a material that may be understood with reference to the relevant description above.

An embodiment of the present invention further provides a surgical assembly, which includes the sheath and the balloon mentioned above, and a balloon catheter, wherein the balloon is arranged at the balloon catheter, and an inner cavity of the balloon is communicated with an inner cavity of the balloon catheter.

In an example, the surgical assembly may be a surgical assembly of percutaneous nephroscopy. In other examples, the surgical assembly may also be a surgical assembly of biliary tract surgery.

Figure 12:
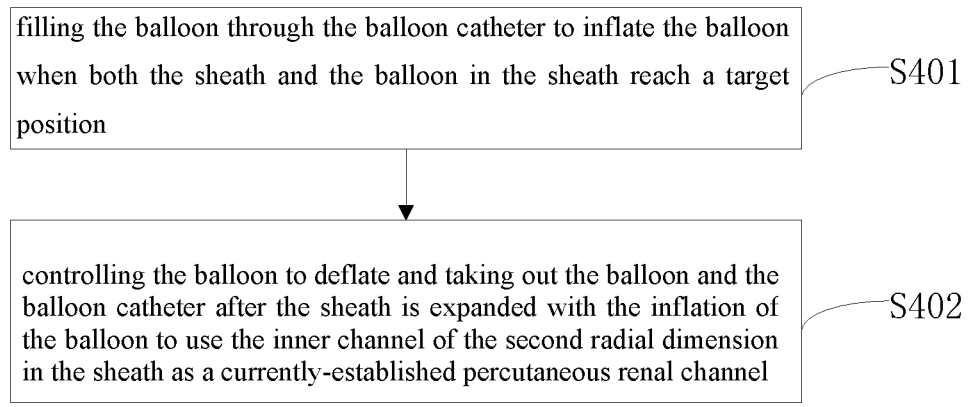
FIG. 12 is a flow chart of a method of using the surgical assembly of percutaneous nephroscopy according to an embodiment of the present invention.

With reference to FIG. 12, an embodiment of the present embodiment further provides a method of using the surgical assembly mentioned above, which includes the following steps:

S401: the balloon is filled through the balloon catheter to cause the balloon to expand when both the sheath and the balloon in the sheath reach a target position;

S402: the balloon is controlled to deflate and the balloon and the balloon catheter are taken out after the sheath is expanded with the inflation of the balloon to use the inner channel of the second radial dimension in the sheath as a currently-established working channel.

The working channel mentioned above may be, for example, a percutaneous renal channel of percutaneous nephroscopy. If applied to other operations, the above steps may also establish other working channels.

It can be seen that the sheath and surgical assembly involved in the embodiment of the present invention may also be applied to other application scenarios besides percutaneous nephroscopy.

In summary, for the sheath, the surgical assembly and the method of using the same provided in the embodiment of the present invention, since the radial size of the sheath is variable, the sheath is facilitated to wrap the balloon and enter the human body when being not expanded, and to expand with the inflation of the balloon after reaching the target position, thereby realizing the establishment of the channel. It can be seen that when the sheath related to the present invention is used, the effect in establishing the working channel and the safety during the establishment process may not be limited to the control of the inflation size of the balloon, thereby effectively guaranteeing the safety and the effect in establishing the channel. Moreover, based on the sheath and the surgical assembly involved in the present invention, the two-step action of expanding and inserting the sheath is facilitated to be changed into one-step action and further to directly establish the working channel after the expansion, thereby simplifying the work process, avoiding secondary damage caused by the two-step action and further improving the safety.

At last, it should be noted that the above various embodiments are only used to describe the technical solutions of the present invention, rather than limiting the technical solutions of the present invention. Even through the present invention is described in detail with reference to the foregoing embodiments, those of ordinary skilled in the art should understand that they can still modify the technical solutions recorded in the foregoing various embodiments or equivalently replace some or all of the technical features. However, these modifications or replacements do not make the essence of the corresponding technical solutions deviate from the scope of the technical solutions of the embodiments of the present invention.

What is claimed is:

1. A sheath, comprising a ring-shaped inner layer structure, a ring-shaped outer layer structure and a frame structure, wherein the outer layer structure is arranged around an outer side of the inner layer structure, and the frame structure is arranged between the inner layer structure and the outer layer structure; the inner layer structure, the frame structure, and the outer layer structure can be radially expanded with the inflation of a balloon inside the inner layer structure;

when the inner layer structure, the frame structure and the outer layer structure are not radially expanded, a radial dimension of an inner channel of the inner layer structure is at a first radial dimension, and the first radial dimension is greater than or equal to a radial dimension of the balloon that is not inflated;

after the inner layer structure, the frame structure, and the outer layer structure are radially expanded, and the balloon is removed or deflated, the radial dimension of the inner channel of the inner layer structure is at a second radial dimension, and the second radial dimension is greater than the first radial dimension, wherein the frame structure comprises at least one ring-shaped or spiral-shaped frame body, the frame body comprises at least one deformable section, a deformation degree of the deformation section is related to a circumferential length of the frame body, wherein the deformable section is an arc line section or a broken line section when the frame body is not expanded, the deformable section is an arc line section or a broken line section when the frame body is expanded, and a length of the deformable section along the circumferential direction of the frame body matches a bending degree or a curving degree of the deformable section, wherein when the frame body is radially expanded, the bending degree or the curing degree of the deformable section becomes lower, and a length of the deformable section along the circumferential direction of the frame body becomes longer, wherein an opening direction of the deformable section matches an axial direction of the frame body, and the opening directions of two adjacent deformable sections in the same frame body are opposite, and wherein the frame structure further comprises a reinforcing rib connected between two adjacent frame bodies, the reinforcing rib is connected to axial end portions of the two deformable sections along the axial direction of the frame body, and the openings of the two deformable sections connected to the reinforcing rib are in opposite directions.

2. The sheath according to claim 1, wherein the frame body formed by connecting a plurality of deformable sections end to end in sequence;
if the deformable section is the broken line section, the frame body has a continuous sawtooth waveform;
if the deformable section is the arc line section, the frame body has a continuous sinusoidal waveform.

3. The sheath according to claim 2, wherein an opening direction of the deformable section matches an axial direction of the frame body, and the opening directions of two adjacent deformable sections in the same frame body are opposite.

4. The sheath according to claim 2, wherein the inner layer structure comprises an inner layer film, and a material of the inner layer film is any one of PTFE, silica gel, or polyurethane material;
the outer layer structure comprises an outer layer film, and a material of the outer layer film is any one of PTFE, silica gel, or polyurethane material.

5. The sheath according to claim 2, wherein a material of the frame structure is at least one of cobalt-based alloy, stainless steel and platinum-chromium alloy;
the frame structure is formed by at least one of the following processes:
laser cutting;
first forming a structure that forms a sine wave or a sawtooth wave that is not in a closed loop by mechanical processing, then welding end to end to form a ring-shaped frame body, and then selecting one or more welding points to weld a plurality of frame bodies together, to form the frame structure;
first forming the spiral-shaped frame body to be required by mechanical processing, and selecting one or more welding points for a plurality of frame bodies together if the number of the spiral-shaped frame body is at least a plurality of frame bodies, to form the frame structure.

6. The sheath according to claim 1, wherein the inner layer structure comprises an inner layer film, and a material of the inner layer film is any one of PTFE, silica gel, or polyurethane material;
the outer layer structure comprises an outer layer film, and a material of the outer layer film is any one of PTFE, silica gel, or polyurethane material.

7. The sheath according to claim 1, wherein a material of the frame structure is at least one of cobalt-based alloy, stainless steel and platinum-chromium alloy;
the frame structure is formed by at least one of the following processes:
laser cutting;
first forming a structure that forms a sine wave or a sawtooth wave that is not in a closed loop by mechanical processing, then welding end to end to form a ring-shaped frame body, and then selecting one or more welding points to weld a plurality of frame bodies together, to form the frame structure;
first forming the spiral-shaped frame body to be required by mechanical processing, and selecting one or more welding points for a plurality of frame bodies together if the number of the spiral-shaped frame body is at least a plurality of frame bodies, to form the frame structure.

8. A surgical assembly, comprising the sheath and the balloon according to claim 1, and a balloon catheter, wherein the balloon is arranged at the balloon catheter, and an inner cavity of the balloon is communicated with an inner cavity of the balloon catheter.

9. A method of using the surgical assembly according to claim 8, comprising:
filling the balloon through the balloon catheter to inflate the balloon when both the sheath and the balloon in the sheath reach a target position;
controlling the balloon to deflate and taking out the balloon and the balloon catheter after the sheath is expanded with the inflation of the balloon to use the inner channel of the second radial dimension in the sheath as a currently-established working channel.

10. The surgical assembly according to claim 8, wherein the frame structure comprises at least one ring-shaped or spiral-shaped frame body, the frame body comprises at least one deformable section, a deformation degree of the deformation section is related to a circumferential length of the frame body.

11. The surgical assembly according to claim 8, wherein the deformable section is an arc line section or a broken line section when the frame body is not expanded, the deformable section is an arc line section or a broken line section when the frame body is expanded, and a length of the deformable section along the circumferential direction of the frame body matches a bending degree or a curving degree of the deformable section, wherein
when the frame body is radially expanded, the bending degree or the curing degree of the deformable section becomes lower, and a length of the deformable section along the circumferential direction of the frame body becomes longer.

12. The surgical assembly according to claim 8, wherein the frame body formed by connecting a plurality of deformable sections end to end in sequence;
if the deformable section is the broken line section, the frame body has a continuous sawtooth waveform;
if the deformable section is the arc line section, the frame body has a continuous sinusoidal waveform.

13. The surgical assembly according to claim 8, wherein an opening direction of the deformable section matches an axial direction of the frame body, and the opening directions of two adjacent deformable sections in the same frame body are opposite.

14. The sheath according to claim 1, wherein the inner layer structure comprises an inner layer film, and a material of the inner layer film is any one of PTFE, silica gel, or polyurethane material;
the outer layer structure comprises an outer layer film, and a material of the outer layer film is any one of PTFE, silica gel, or polyurethane material.

15. The sheath according to claim 1, wherein the inner layer structure comprises an inner layer film, and a material of the inner layer film is any one of PTFE, silica gel, or polyurethane material;
the outer layer structure comprises an outer layer film, and a material of the outer layer film is any one of PTFE, silica gel, or polyurethane material.

16. The sheath according to claim 1, wherein a material of the frame structure is at least one of cobalt-based alloy, stainless steel and platinum-chromium alloy;
    the frame structure is formed by at least one of the following processes:
    laser cutting;
    first forming a structure that forms a sine wave or a sawtooth wave that is not in a closed loop by mechanical processing, then welding end to end to form a ring-shaped frame body, and then selecting one or more welding points to weld a plurality of frame bodies together, to form the frame structure;
    first forming the spiral-shaped frame body to be required by mechanical processing, and selecting one or more welding points for a plurality of frame bodies together if the number of the spiral-shaped frame body is at least a plurality of frame bodies, to form the frame structure.

\* \* \* \* \*